(12) United States Patent
Popescu

(10) Patent No.: US 7,623,617 B2
(45) Date of Patent: Nov. 24, 2009

(54) METHOD FOR SCATTERED RADIATION CORRECTION OF A CT SYSTEM HAVING AT LEAST TWO FOCUS/DETECTOR SYSTEMS ARRANGED WITH AN ANGULAR OFFSET, AND A CT SYSTEM

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 381 days.

(21) Appl. No.: 11/790,763

(22) Filed: Apr. 27, 2007

(65) Prior Publication Data

US 2007/0253525 A1 Nov. 1, 2007

(30) Foreign Application Priority Data

Apr. 28, 2006 (DE) ................. 10 2006 019 920

(51) Int. Cl.
*A61B 6/03* (2006.01)
(52) U.S. Cl. ............................... 378/7; 378/9
(58) Field of Classification Search .............. 378/7, 378/9
See application file for complete search history.

(56) References Cited

U.S. PATENT DOCUMENTS

| 5,450,462 | A | * | 9/1995 | Toth et al. ................. 378/16 |
|---|---|---|---|---|
| 6,198,790 | B1 | | 3/2001 | Pflaum |
| 6,421,512 | B2 | | 7/2002 | Watanabe et al. |
| 6,744,846 | B2 | | 6/2004 | Popescu et al. |
| 6,876,719 | B2 | * | 4/2005 | Ozaki ............................ 378/7 |
| 7,145,980 | B2 | * | 12/2006 | Sakaguchi et al. ............ 378/7 |
| 2004/0062341 | A1 | | 4/2004 | Popescu et al. |
| 2004/0079232 | A1 | * | 4/2004 | Groh et al. ....................... 96/1 |
| 2005/0089134 | A1 | | 4/2005 | Bruder et al. |

FOREIGN PATENT DOCUMENTS

| DE | 102 32 429 B3 | 1/2004 |
|---|---|---|
| DE | 10 2005 048 397 A1 | 4/2007 |
| WO | WO 03/058222 A2 | 7/2003 |

OTHER PUBLICATIONS

Bruder et al., Design Considerations in cardiac CT, Mar. 2006, SPIE, vol. 6142, pp. 61420H-1-61420H-13.*

* cited by examiner

*Primary Examiner*—Edward J Glick
*Assistant Examiner*—John M Corbett
(74) *Attorney, Agent, or Firm*—Harness, Dickey & Pierce, P.L.C.

(57) ABSTRACT

A method is disclosed for scattered radiation detection and/or for scattered radiation correction. In at least one embodiment, each radiation produced is provided with an individual temporal marker/variation of known magnitude, the change in the measured radiation being investigated for these typical temporal variations, and the fraction of the scattered radiation is inferred from the temporal variation found and, if appropriate, a corresponding correction is carried out. Furthermore, a CT system is disclosed, including a computer program that carries out at least one embodiment of the method.

22 Claims, 4 Drawing Sheets

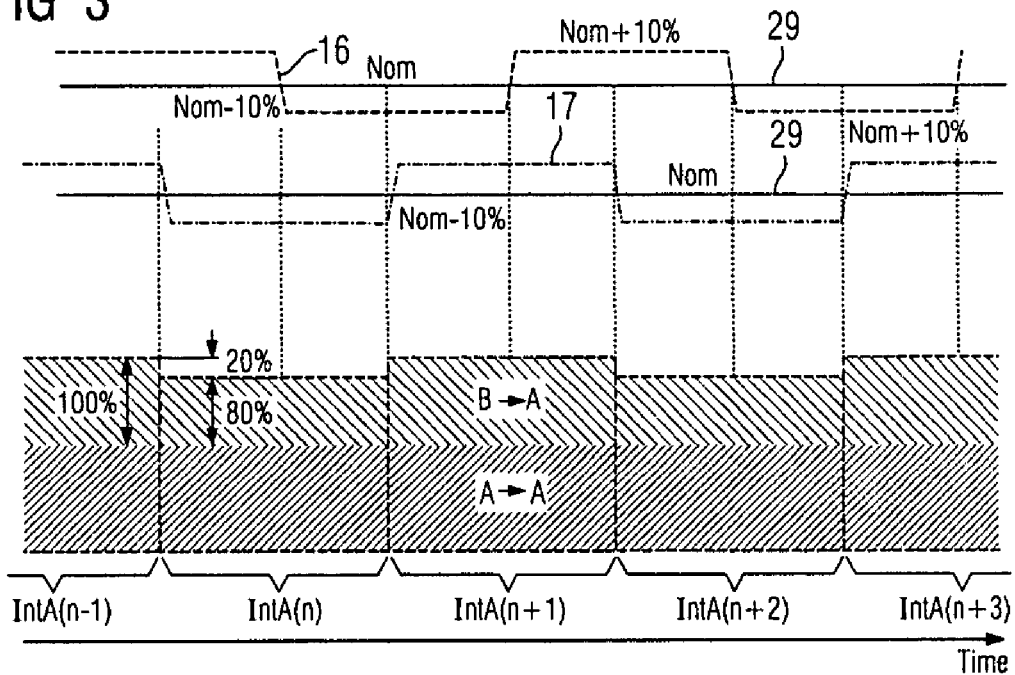
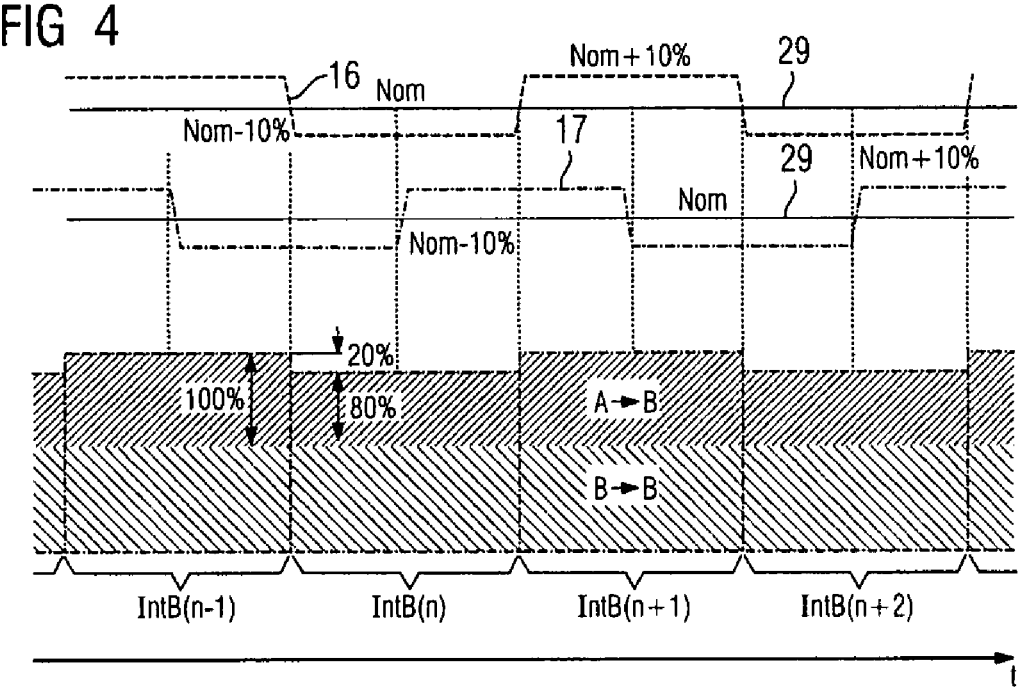

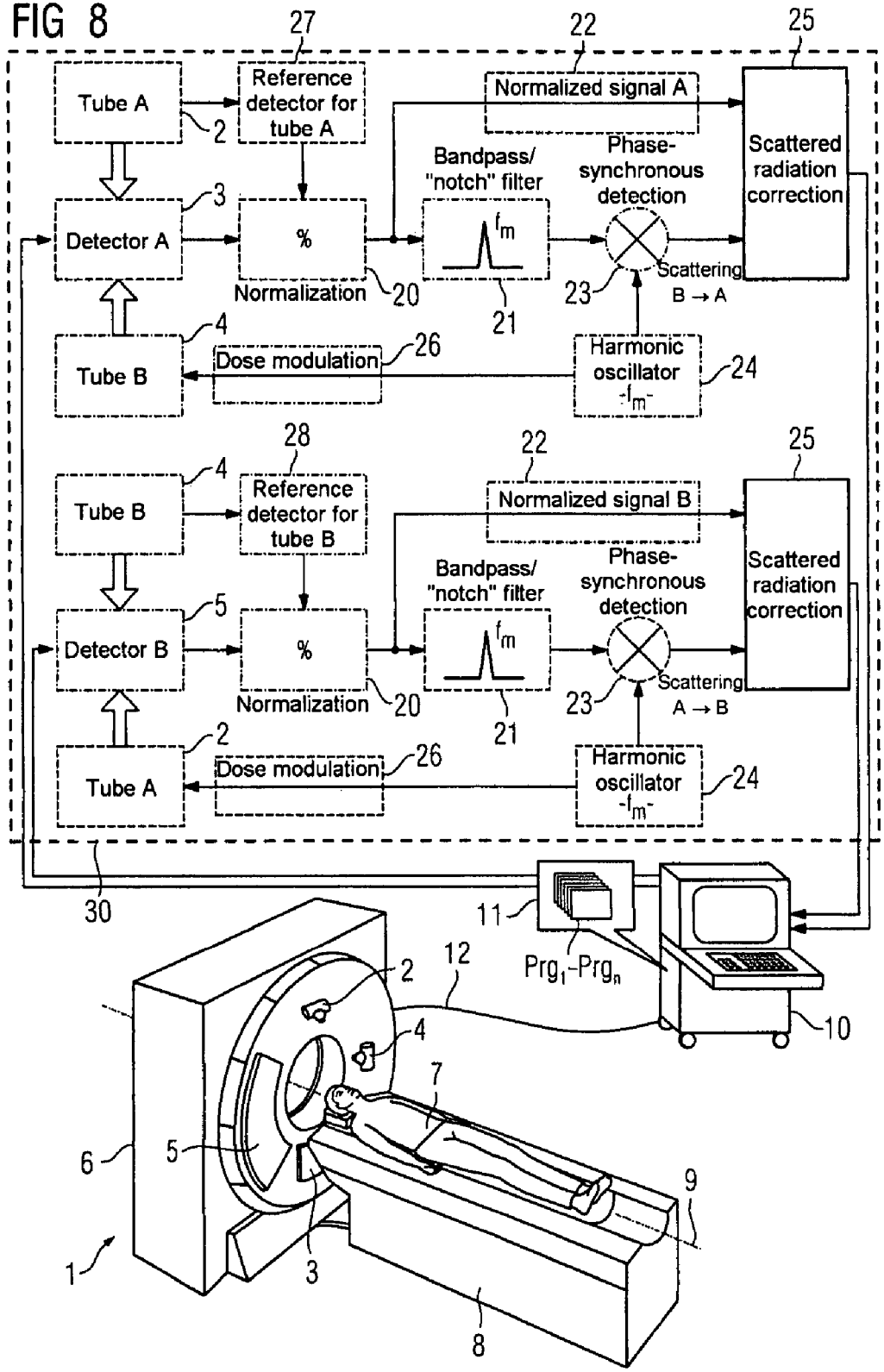

though it is not required, it is preferable that the two or more focus/detector systems are actively operated simultaneously during the scan. The method includes the following method steps:

METHOD FOR SCATTERED RADIATION CORRECTION OF A CT SYSTEM HAVING AT LEAST TWO FOCUS/DETECTOR SYSTEMS ARRANGED WITH AN ANGULAR OFFSET, AND A CT SYSTEM

PRIORITY STATEMENT

The present application hereby claims priority under 35 U.S.C. §119 on German patent application number DE 10 2006 019 920.0 filed Apr. 28, 2006, the entire contents of which is hereby incorporated herein by reference.

FIELD

Embodiments of the invention generally relate to a method for scattered radiation correction of a CT system having at least two simultaneously operated focus/detector systems arranged with an angular offset from one another on a rotatable gantry. For example, they may relate to one wherein, in order to scan an object, the focus/detector systems arranged angularly offset from one another scan the object by virtue of the fact that they rotate about a system axis of the CT system, and absorption values are determined, for a multiplicity of individual rays, from the measured ratio of the measured radiation intensity to the nonattenuated radiation intensity, the measured values are subjected to scattered radiation correction, and CT pictures or CT volume data of the object are reconstructed with the aid of the determined absorption data.

BACKGROUND

It is known in principle that during CT examinations scattered radiation effects are produced that lead to inaccuracies in the measurement of the absorption of x-radiation. Looking first at this effect in unifocal detector systems, the problem of scattered radiation here becomes larger the wider the beam fan used is expanded, since the sites at which scattered radiation is produced increase correspondingly.

In the case of such CT systems, this known effect is counteracted by fitting in front of the detector so-called scattered radiation collimators that expose in front of each detector element only the direct radiation direction between detector element and focus, and largely shade all the other directions. Such scattered radiation collimators are also used with the bifocal or multifocal detector systems. However, these scattered radiation collimators cannot diminish the scattered radiation that is produced by beams of another focus arranged with an angular offset and has the same spatial orientation as the actual direct beam that originates from a focus opposite the detector and whose intensity is to be measured.

There is thus in principle the problem of determining the fraction of this scattered radiation in the total measured intensity of the radiation, and of correcting the measured radiation intensity by this fraction.

A similar method for scattered radiation correction in a bifocal detector system is disclosed, for example, in patent specification DE 102 32 429 B3. In the case of this patent specification, two focus/detector systems arranged angularly offset from one another are operated in an alternating fashion at least temporarily, such that the scattered radiation actually occurring that originates from the focus/detector system being operated can be measured directly in the focus/detector system respectively not switched on. In order to carry out this method, it is necessary to operate the X-ray sources in an alternating fashion at least partially, as a result of which at these times image information from the CT scan is lacking at least in the detector of the X-ray tube that is not being operated, and so gaps are produced in the data acquisition.

In this variant of the operation, there is the problem that the scanning during the alternating switching on/switching off of the tube or the radiation is not complete and exhibits gaps.

SUMMARY

In at least one embodiment, the invention is directed to an improved method for scattered radiation correction of a CT system having at least two focus/detector systems arranged with an angular offset from one another. In at least one embodiment, the method on the one hand leads to a complete scanning devoid of gaps, but on the other hand measures the actually occurring scattered radiation of the currently scanned object.

The inventor has realized, in at least one embodiment, that in the case of at least two focus/detector systems arranged with an angular offset, it is possible for the scattered radiation fractions both to be identified and quantitatively detected in mutual fashion per focus/detector system by an individual and known modulation of the radiation intensity, the modulation of the radiation intensity varying in an intensity range in which a measurable scanning is achieved even with the minimum values. This produces no temporal gaps in the scanning of the at least two focus/detector systems, since an adequate photon flux is present for a measurement even given the minimum radiation intensity used.

Thus, in accordance with the idea of at least one embodiment of the invention, there is modulated onto each individual focus/detector system a change in radiation intensity of a specific frequency or a specific phase the character of which is sufficient to be able to detect this component of the scattered radiation on the basis of this individual modulation of the radiation intensity in the respective other focus/detector system or the respective other focus/detector systems which contribute to the scattered radiation of a focus/detector system. This can happen, on the one hand, by virtue of the fact that the modulation of the radiation in the focus/detector system being considered is undertaken in such a way that it remains unobserved there, while the modulation of the other focus/detector system(s) can be identified. For example, consideration can be given here to a specific synchronization with the scanning rate at which the individual detector elements of the detector are scanned.

However, it is also possible to equip the modulation of the radiation intensities with different frequencies or phase shifts that render them individually detectable. If, on the other hand, the degree of modulation of the radiation intensity of a specific focus/detector system is known, this known degree of modulation can be used to directly infer how high is the component of the scattered radiation in the total radiation that is caused by the radiation thus modulated.

If, for example, the radiation in a system A is modulated by ±10%, while in another focus/detector system, in turn, a variation of the radiation intensity by ±1% is measured, the scattered radiation fraction must be 10% when viewed approximately. Of course, this calculation must be carried out with mathematical accuracy in practice.

In accordance with this basic idea, in at least one embodiment, the inventor proposes a method for scattered radiation correction of a CT system that is equipped with at least two simultaneously operated focus/detector systems arranged with an angular offset from one another on a rotatable gantry and having in each case one focus and one assigned detector receiving the direct radiation of this focus, wherein X-radiation is produced in each of the at least two focus/detector systems in an X-ray tube by a tube current with a tube voltage, in order to scan an object the focus/detector systems arranged angularly offset from one another scan the object, with the aid of the X-radiation produced, by virtue of the fact that they rotate about a system axis of the CT system, and absorption values are determined, for the multiplicity of individual rays in space, from the measured ratio of the measured radiation intensity to the nonattenuated radiation intensity of the individual rays, wherein the measured values are subjected to scattered radiation correction, and CT pictures or CT volume data of the object are reconstructed with the aid of the determined absorption data.

An inventive improvement of at least one embodiment of the method resides in that the radiation intensity of the emitted radiation of each focus/detector system is varied individually as a function of time by a mean value of greater than 50% of the maximum radiation intensity, and in the respectively assigned detector the scattered radiation fraction of other nonassigned focus/detector systems is determined by virtue of the fact that either their individual temporal variation of the radiation intensity does not correspond to the assigned focus/detector system, or their individual temporal variation of the radiation intensity corresponds to a nonassigned focus/detector system, that is to say a potential system producing scattered radiation.

With reference to at least one embodiment of the basic inventive method outlined above, there are different variants within the scope of the invention that utilize this fundamental principle.

On the one hand, at least one embodiment of the inventive method can be set out to the effect that precisely two focus/detector systems with the same scanning frequency are used, the radiation intensities of the two focus/detector systems are varied with the aid of the same function and period, these periods being identical to the period of the scanning frequency of the detectors of the focus/detector systems, and the periods of the variation in the radiation intensities and scanning frequencies of the focus/detector systems are offset from one another by an integral multiple of $\pi/2$ and are of synchronous design within a focus/detector system.

Thus, in the case of such a variant, additional use is made of the property of the focus/detector systems that the individual detectors located there, or detector elements thereof are regularly scanned at a specific scanning frequency, the scanning behavior and the variation in radiation of the individual detector systems being tuned to one another such that in each case the variation respectively undertaken in the radiation intensities in the focus/detector system in which the radiation is used for direct scanning is equalized over the scanning period, while the radiation intensities that are generated by the other focus/detector system producing scattered radiation generate a direct modulation of the measured radiation. Once this fraction is determined, the level of the variation in the radiation intensity is known from the focus/detector system producing scattered radiation, and so it is possible to infer the actually measured fraction of scattered radiation directly.

It is particularly advantageous here when the radiation intensity of the emitted radiation of the focus/detector systems is temporally varied by a mean value of greater than 80%, preferably greater than 90%, of the maximum radiation intensity. Owing to this measure, the radiation intensity maintains over the entire duration of the scan an order of magnitude in the case of which no gaps arise in the scanning, and so no artifacts or defects occur.

According to at least one embodiment of the invention, it is proposed with reference to the temporal variation in the radiation intensity that the latter can run trapezoidally around a mean value. However, there is also the possibility of causing this radiation intensity to vary sinusoidally, or of selecting similar forms of the variation.

In a concrete design of at least one embodiment of the above-described method, the inventor also proposes that in the event of a variation in the radiation intensity of the nonassigned focus/detector system by ±x %, and of a measured difference ±y % in the radiation intensity between neighboring detector elements, the scattered radiation fraction z % is calculated with the aid of $$z\ \% = \frac{x\ \%}{y\ \%}.$$

In another variation of at least one embodiment, referred to the same detector element in the event of a variation in the radiation intensity of the nonassigned focus/detector system by ±x %, and of a measured radiation intensity $SA_n^i$ of an nth scanning period, the scattered radiation fractions $OS^i_{B \to A}$ can be calculated with the aid of:

$$OS^i_{B \to A} = (SA_n^i - SA_{n-1}^i) \cdot \frac{100 - 2 \cdot x}{2 \cdot x}$$

or $$OS^i_{B \to A} = (SA_n^i - SA_{n+1}^i) \cdot \frac{100 - 2 \cdot x}{2 \cdot x}$$

for scanning periods and/or integration periods with a positive variation in the radiation intensity, and $$OS^i_{B \to A} = (SA_{n-1}^i - SA_n^i) \cdot \frac{100}{2 \cdot x}$$

or $$OS^i_{B \to A} = (SA_{n+1}^i - SA_n^i) \cdot \frac{100}{2 \cdot x}$$

for scanning periods and/or integration periods with a negative variation in the radiation intensity, i representing a serial number for the detector elements considered, and n representing the number of temporally consecutive scanning periods.

It may be pointed out that the detector systems A and B are interchangeable with reference to the respective calculation of the scattered radiation intensity.

In another variant of at least one embodiment, which by contrast with the previously described time-oriented consideration of the variation, is space-oriented, the inventor proposes that referred to the same scanning period in the event of a variation in the radiation intensity of the nonassigned focus/detector system by ±x %, and of a measured radiation intensity $SA_n^i$ of the nth detector element $E_n$, and of a measured radiation intensity $SA_{nn}^i$ of a neighboring detector element $E_{nn}$ with a differently directed variation in the radiation intensity, the scattered radiation fractions $OS^i_X \to Y$ from the first focus/detector system X to the second focus/detector system Y are calculated with the aid of:

$$OS^i_{X \to Y} = (SA^i_n - SA^i_{nn}) \cdot \frac{100 - 2 \cdot x}{2 \cdot x}$$

or $$OS^i_{X \to Y} = (SA^i_n - SA^i_{nn}) \cdot \frac{100 - 2 \cdot x}{2 \cdot x}$$

for scanning periods and/or integration periods with positive variation in the radiation intensity, and $$OS^i_{X \to Y} = (SA^i_{nn} - SA^i_n) \cdot \frac{100}{2 \cdot x}$$

or $$OS^i_{X \to Y} = (SA^i_{nn} - SA^i_n) \cdot \frac{100}{2 \cdot x}$$

for scanning periods and/or integration periods with a negative variation in the radiation intensity, i representing a serial number for the detector elements considered.

In the case of the above-described variants, a variation in the radiation intensities may be carried out with the scanning frequency, the focus/detector systems being operated in a fashion offset by $\pi/2$ with reference to their phase relative to the directly irradiated detector, and with the same phase or in a fashion offset by $\pi$ with reference to the respective other detector.

A fundamentally different type of design for at least one embodiment of the inventive method resides in that the variation in the radiation intensity runs over a number of integration periods of the detectors, the association of the fraction and size of the fraction of the scattered radiation produced being determined with the aid of appropriate filters or digital signal processing.

The inventor proposes in accordance with this idea that at least one embodiment of the inventive method be configured to the effect that, in the case of at least two focus/detector systems, the radiation intensities of the focus/detector systems are varied with the same frequencies but different phase, in at least one detector element the variation in the radiation intensity is detected in the respectively indirectly irradiated detector system of at least one focus/detector system with another phase belonging to another focus/detector system, and the scattered radiation fraction in this focus/detector system is determined on the basis of the detected radiation with the other phase and of the known fraction of the variation in the generated radiation intensity with this phase. Thus, in this variant of at least one embodiment, the magnitude of the variation in the radiation is on the one hand determined by the scattered radiation fraction, and is compared with the known percentage of the variation in the scattered radiation from the respective other focus/detector system, the detection being determined by the mutual phase shift in the radiation variation of the two focus/detector systems.

It is possible here for the frequency of the variation in the radiation intensity to be lower, preferably lower by at least the factor 3, than the scanning frequencies of the detector systems.

A further variant of at least one embodiment provides that precisely two focus/detector systems are used, and the phase shift between the frequencies of the variation in the radiation intensity is an integral multiple of $\pi/2$.

Alongside this phase-referred detection of the scattered radiation fraction, there is also the possibility of detecting the scattered radiation with reference to frequency. It is proposed for this purpose that in the case of at least two focus/detector systems the radiation intensities of the focus/detector systems are varied with incommensurable frequencies, in at least one detector element the variation in the radiation intensity is detected in the respectively indirectly irradiated detector system of at least one focus/detector system with another frequency belonging to another focus/detector system, and the scattered radiation fraction in this focus/detector system is determined on the basis of the fraction of the detected radiation with the other phase and of the other known fraction of the variation in the generated radiation intensity with this phase.

Here, as well, the inventor proposes, in at least one embodiment, to design the frequency of the variation in the radiation intensity to be lower, preferably lower by at least a factor of 3, than the scanning frequencies of the detector systems.

It is likewise proposed, in at least one embodiment, to use precisely two focus/detector systems. In a particularly advantageous embodiment of the inventive method that operates with slower frequencies and in which the scattered radiation is detected with reference to phase and/or frequency, it is proposed that for each focus/detector system there take place a monitoring of the direct radiation, preferably directly at the X-ray tube, and a normalization of the measurements to this direct radiation.

It is also proposed that the radiation intensity of the emitted radiation of the focus/detector systems is temporally varied by a mean value of greater than 80%, preferably greater than 90%, of the maximum radiation intensity.

The temporal variation in the radiation intensity of the focus/detector systems can, for example, run trapezoidally or sinusoidally or in another uniformly recurring fashion about the mean value.

In order to avoid excessively large spatial fluctuations, the inventor also proposes, in at least one embodiment, that the determined correction values of the above-described method and/or the measured values that lead to determination of the correction values are averaged over a number of scanning periods. Additionally or alternatively, these values can also be averaged over a certain detector area, that is to say over a number of neighboring detector elements. This averaging can be done in rowwise or areawise fashion, for example over 2×2, 3×3 or 4×4 pixels, without limiting the generality.

It is expressly pointed out that the above-described embodiments of the method are not limited to bifocal detector systems, but that they are also within the scope of the invention to transfer this method correspondingly to trifocal or multifocal detector systems as well.

The inventor further proposes, in at least one embodiment, that the temporal variation in the radiation intensity of the focus/detector systems is undertaken by a variation in the tube current or by a variation in the accelerating voltage at the X-ray tube, the variation in the accelerating voltage being more advantageous, particularly when use is made of high frequencies, since the design dictates that the tube current reacts substantially more sluggishly than the accelerating voltage can be varied.

BRIEF DESCRIPTION OF THE DRAWINGS

The invention is described in more detail below using the example embodiments and with the aid of the figures, only the features required for understanding the invention being illustrated. The following reference numerals are used here: 1: CT system; 2: first X-ray tube (system A); 3: first detector (system A); 4: second X-ray tube (system B); 5: second detector (system B); 6: gantry housing; 7: patient; 8: movable patient couch; 9: system axis; 10: control/arithmetic logic unit; 11: memory; 12: first beam (system A); 13: scattered radiation to the second detector from the first beam; 14: second beam (system B); 15: scattered radiation to the first detector from the second beam; 16: dose rate profile of the first X-ray tube (system A); 17: dose rate profile of the second X-ray tube (system B); 18: integration periods of the first detector (system A); 19: integration periods of the second detector (system B); 20: normalization step; 21: bandpass filter; 22: normalized detector signals; 23: phase-synchronous detection; 24: harmonic oscillator; 25: scattered radiation correction; 26: dose rate modulation; 27: monitoring of the dose rate at the first X-ray tube (system A); 28: monitoring of the dose rate at the second X-ray tube (system B); 29: nominal value/mean value of the dose rate; 30: method scheme for scattered radiation correction; $D_A$: detector of system A; $D_B$: detector of system B; $\dot{D}(t)$: temporally varying radiation intensity; $E_n$: detector elements; $F_A$: focus of system A; $F_B$: focus of system B; $f_A$: scanning frequency of system A; $f_B$: scanning frequency of system B; $FDS_A$: focus/detector system of system A; $FDS_B$: focus/detector system of system B; $I_A$: tube current of system A; $I_B$: tube current of system B; $OS^i_{B \to A}$: scattered radiation fraction of the X-ray tube of system B in the detector of system A of scanning period n in the detector channel i; $p_A$: period of system A; $p_B$: period of system B; $Prg_x$: computer program; $SA_n$: total radiation intensity in the detector of system A in the scanning period n; $SA_n^i$: radiation intensity in the detector of system A in the scanning period n in the detector channel i; $U_A$: tube voltage of system A; $U_B$: tube voltage of system B; $f_A$: phase of system A; $f_B$: phase of system B; $v_A$: frequency of system A; $v_B$: frequency of system B.

In detail:

FIG. 3 shows the effect of the phase-offset dose rate profiles on the detected dose in detector system A;

FIG. 4 shows the effect of the phase-offset dose rate profiles on the detected dose in detector system B;

FIG. 8 shows a CT system with two focus/detector systems arranged with an angular offset.

DETAILED DESCRIPTION OF THE EXAMPLE EMBODIMENTS

Figure 1:
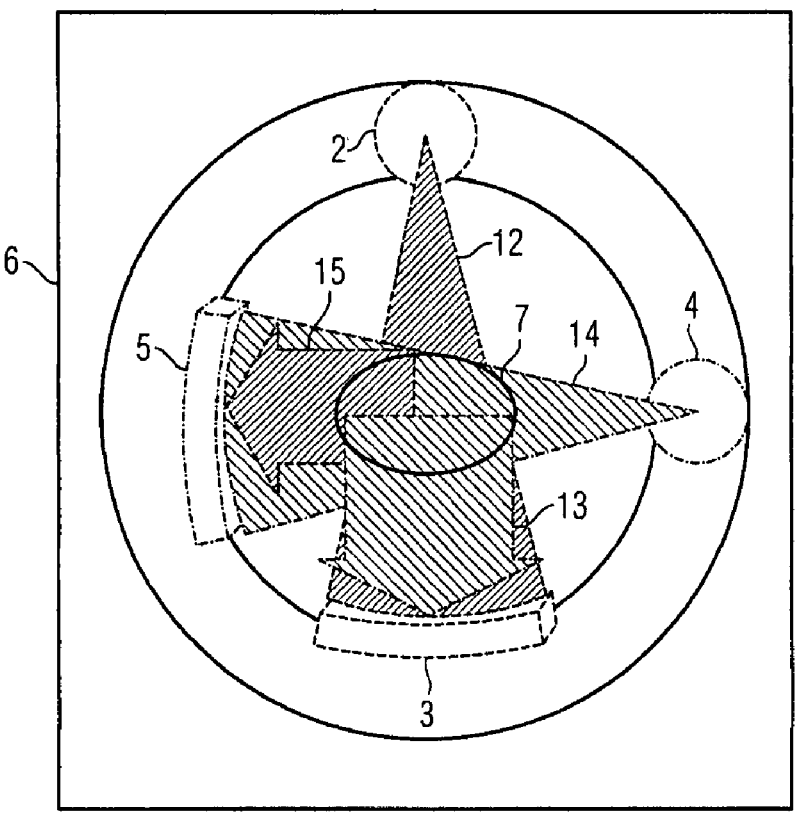
FIG. 1 is a schematic of the direct and scattered radiation of two angularly offset focus/detector systems.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows a schematic representation of a computer tomograph with a section through a gantry housing having two focus/detector systems arranged with an angular offset of 90°, the first focus/detector system having an X-ray tube 2 and an opposite detector 3, and the second focus/detector system having an X-ray tube 4, likewise arranged on the gantry, with an opposite detector 5. The focus/detector system with the X-ray tube 2 and the detector 3 is to be referred to below as the "A" system, and the angularly offset focus/detector system with the X-ray tube 4 and the detector 3 is to be referred to as the "B" system. Illustrated emanating from the X-ray tube 2 is the beam 12 that leads to the opposite detector 3, while a beam 14 is guided from the X-ray tube 4 to the detector 5 opposite this tube. Located in the scanning area of the two focus/detector systems A and B is a patient 7 at which the respective beam interacts and produces a scattered radiation that is measured by the detector not directly irradiated.

Thus, the beam 14 produces a scattered radiation 13 that is measured at the detector 3, while the beam 12 produces a scattered radiation 15 that is measured by the detector 5. The result of this is the corruption of the absorption data that is known to be determined by the ratio between the radiation intensity with and without the patient 7, such that the additionally detected scattered radiation of the respective other focus/detector system simulates a diminished absorption.

An aim of an embodiment of the invention is thus to find a system in the case of which the fraction of the scattered radiation can be detected from the respective focus/detector system arranged with an angular offset, such that the magnitude of the absorption actually taking place is detected without corrupting effects owing to striking scattered radiation from the respective other focus/detector system.

An important problem resides here in that it is not always the same object, but different objects, that is to say different patients, that are being scanned, and so different scattered radiation fractions also arise from object to object on the basis of the constantly changing geometric conditions. The methods known in the prior art in accordance with which, for example, the scattered radiation is determined by measurements at phantoms are therefore only conditionally suitable for defining the actual scattered radiation fractions.

It is therefore proposed according to an embodiment of the invention also to provide each focus/detector system with a unique property that also influences the scattered radiation such that it is possible to use current measurements to establish which fraction of the radiation that is measured at the respective detector originates from the opposite tube, or originates from an X-ray tube arranged angularly offset therefrom, and can thus be judged to be scattered radiation. As individual property, the respective radiations of the different focus/detector systems can also be given a specific frequency and/or phase shift in the dose variation, the magnitude of the dose variation being known in the respective focus/detector system. The fraction of direct radiation and/or the fraction of the measured scattered radiation can thereby be directly determined on the basis of these known properties.

Figure 2:
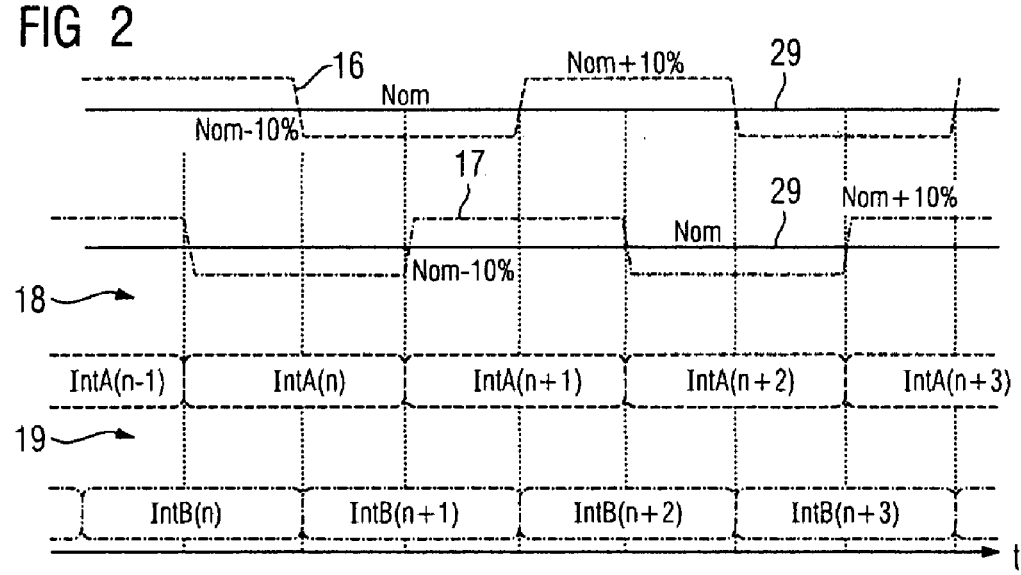
FIG. 2 shows dose rate profiles and integration periods of the two focus/detector systems from FIG. 1.

To this end, the inventor proposes in a preferred example as illustrated in FIG. 2 to vary the dose rate profile of the two X-ray tubes in accordance with FIG. 1 by ±10%, there being a phase offset between the two focus/detector systems of $\pi/2$. The frequency of the dose rate variation is attuned in this case in such a way that it is identical to the scanning rate of the detector systems, there likewise being a phase offset of $\pi/2$ between the frequency of the dose of a focus/detector system and the scanning rate, such that the dose rate variation in the directly irradiated detector is averaged out in each case in an integration period of the detector or of the detector elements of the detector, while the radiation fraction arriving as scattered radiation at the detector arranged with an angular offset runs synchronously with the integration period of the detector arranged with an angular offset such that the change in dose is measured in full.

FIG. 2 shows a first dose rate profile 16 of the focus/detector system A which exhibits a 10% variation about the nominal value, illustrated by the line 29. Shown therebelow is the dose rate profile 17 of the focus/detector system B arranged with an angular offset of 90°, which runs with a phase offset of $\pi/2$ in relation to the dose rate profile 16. Shown therebelow, in turn, are the integration periods of the detector A and, therebelow, of the detector B, the time axis t running from left to right. Looking, now, at the dose rate profile 16 with the integration periods 18 of the focus/detector system A, it is to be seen from the trapezoidal profile and the phase shift between the dose rate profile 16 and the integration periods 18 that the variation in the dose rate over the entire integration period of the directly irradiated detector is averaged out such that a uniform dose rate averaged over the integration periods appears for the respectively directly irradiated detector.

The same situation holds for the dose rate profile 17 and the integration periods 19 of the focus/detector system B. However, looking at the effect of the dose rate profile 16 on the integration periods 19, that is to say the change in intensity, that is transmitted by the scattered radiation from the focus A onto the detector system B, it is to be seen that owing to the fact that the variations run in phase with the integration periods of the detector system arranged with an angular offset the change in the dose rate profile 16 in the detector system B comes through at 100%.

This situation is illustrated once again separately in FIGS. 3 and 4 for each focus/detector system A and B.

Illustrated at the top in FIG. 3 is the dose rate profile 16 with a 10% fluctuation about a nominal value 29, while the dose rate profile 17 of the focus/detector system B producing scattered radiation is plotted therebelow. The integration periods of the detector from the focus/detector system A are illustrated therebelow, the integrated-out dose fraction from the directly irradiated focus being shown below in the portion hatched from bottom left to top right, while the scattered radiation fraction is shown above with hatching from top left to bottom right. The previously described phase offset between the integration periods and the dose variation of the directly irradiating focus A causes a variation in the direct radiation fraction via the integration period. A precondition of this is, of course, that there should also be no changes, or only minimal ones, in the absorption over the integration periods. However, in the case of the scattered radiation fraction illustrated in the upper part a variation of ±20% occurs in the overall scattered radiation fraction.

The same situation is illustrated in FIG. 4 for the focus/detector system B.

Assuming that there are no large changes in the measured absorption between the integration periods—it is now possible by comparing two neighboring integration periods of a detector element to determine the fraction of the scattered radiation in the overall measured radiation on the basis of the known variation conditions. If, moreover, averaging is carried out over a number of integration periods or over a small detector field, for example 2×2, 3×3 or 4×4 pixels, possible fluctuations are equalized.

Figure 5:
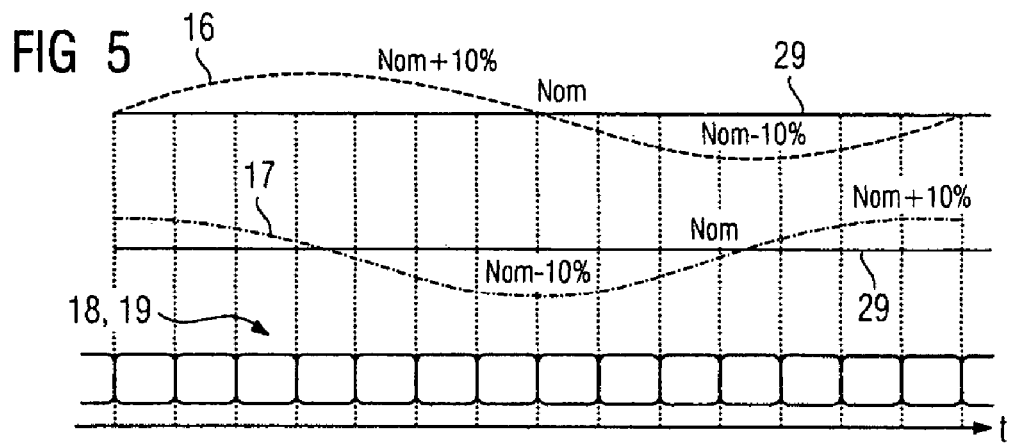
FIG. 5 is a schematic of a phase-shifted dose rate variation of two focus/detector systems with a lower frequency as against the integration periods of the detector systems.

Another possibility for determining the scattered radiation fraction from the direct measurements of a number of focus/detector systems arranged with an angular offset is illustrated in FIG. 5. Here, the two dose rate profiles 16 and 17 are illustrated with a substantially lower frequency as against the integration periods 18, 19 of the detectors of the focus/detector systems A and B, the integration periods in this variation being arranged with the same phase over the two focus/detector systems. The basic idea here consists in that the variations in the radiation intensity in the two focus/detector systems are balanced out by monitor measurements in which scattered radiation can be excluded, and so only the variation in the scattered radiation is measured as variation in dose.

Figure 6:
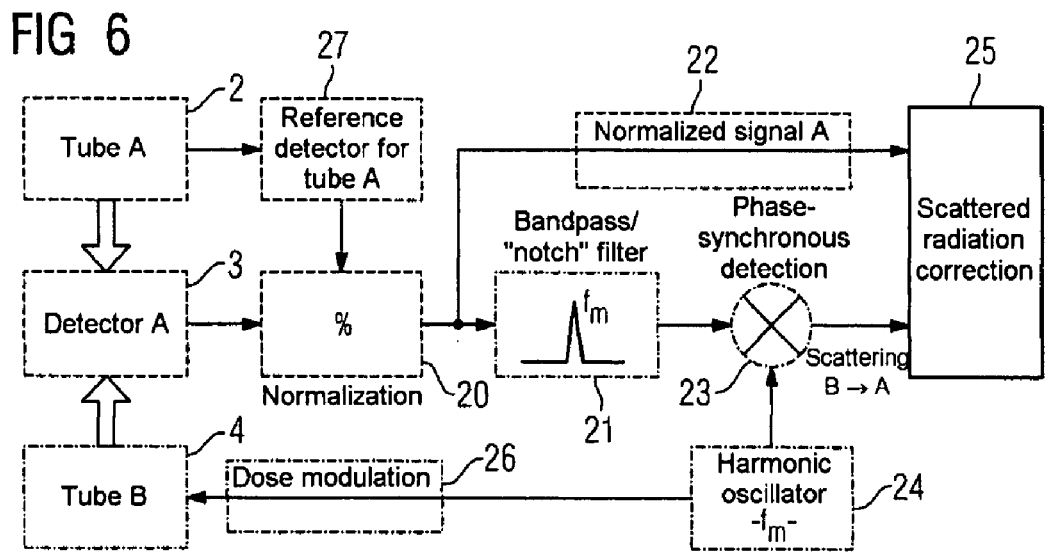
FIG. 6 shows a method scheme for scattered radiation correction of the focus/detector system A.
Figure 7:
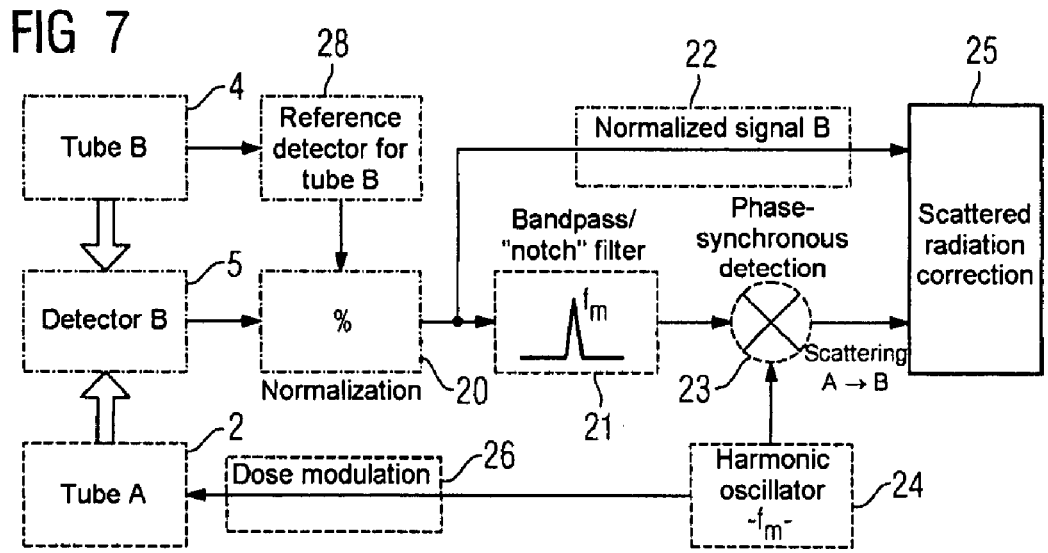
FIG. 7 shows a method scheme for scattered radiation correction of the focus/detector system B.

The two sequence diagrams of the two measuring paths for the focus/detector systems A and B are illustrated in FIGS. 6 and 7, these flowing identically in principle "with reversed signs".

FIG. 6 shows the method sequence for the focus/detector system A. Here, the detector 3 is irradiated directly starting from the X-ray tube 2, the variation in the dose rate in system A being measured via a reference detector 27, and a corresponding normalization taking place in method step 20. Following on from method step 20, the normalized signal is led via a bandpass filter 21 of narrow bandwidth such that only the signal components with the corresponding frequency are passed on to a phase-synchronous detection 23 where it is only the signals corresponding to the phase of the focus/detector system B producing scattered radiation that are determined. To this end, the frequency generated by a harmonic oscillator 24 is passed on to the phase-synchronous detection 23, which is also used for the dose modulation 26 in the X-ray tube 4 producing scattered radiation. The two items of information comprising the normalized signal 22 of the direct radiation and the fraction of the scattered radiation are used in step 25 to determine the scattered radiation fraction, a corresponding correction being carried out in the step.

FIG. 7 shows the corresponding situation to FIG. 6, but for the focus/detector system respectively having an angular offset.

An example design of a computed tomography system that applies the inventive method of scattered radiation correction in accordance with FIGS. 6 and 7 is illustrated in FIG. 8.

This shows in a 3D schematic a CT system 1 that has two focus/detector systems with an angular offset of 90°, the first focus/detector system including an X-ray tube 2 and a detector 3, and the second focus/detector system including an X-ray tube 4 and an oppositely arranged detector 5. The two focus/detector systems are arranged on a gantry (not illustrated in more detail here) in a gantry housing 6. The entire CT system is controlled by an arithmetic and control unit 10 where, in addition to the control, the corresponding evaluation, in particular also the scattered radiation correction, takes place with the aid of the programs $Prg_1$ to $Prg_n$ included in the memory 11.

To be scanned, a patient 7 is pushed through an opening in the gantry housing along the system axis 9 with the aid of a movable patient couch, while the two focus/detector systems scan this patient 7 in a rotating fashion. The scattered radiation arising during this scanning in the respective focus/detector system arranged with an angular offset is detected by appropriate computer programs, as previously described, and a corresponding scattered radiation correction such as is illustrated schematically in the box 30 is carried out.

In this case, the dose rate of the focus/detector systems is influenced such that an individual impression arises that has an effect on the scattered radiation—which is produced in proportion to the direct irradiation. A statement relating to the percentage fraction of the scattered radiation in the entire measured radiation in the respective detector system can be made subsequently on the basis of the known magnitude of the variation.

It goes without saying that the abovementioned features of embodiments of the invention can be used not only in the respectively specified combination, but also in other combinations or on their own, without departing from the scope of the invention.

Overall, at least one embodiment of the invention thus presents a method for scattered radiation detection and/or for scattered radiation correction in which each radiation produced is provided with an individual temporal marker/variation of known magnitude, the change in the measured radiation is examined for these typical temporal variations, and the fraction of the scattered radiation is deduced from the temporal variation found, and a corresponding correction is carried out, if appropriate.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for scattered radiation correction of a CT system including at least two simultaneously operated focus/detector systems arranged with an angular offset from one another on a rotatable gantry, each including one focus and one assigned detector to receive direct radiation of the focus, the method comprising:

producing X-radiation in each of the at least two focus/detector systems in an X-ray tube by a tube current with a tube voltage;

arranging the focus/detector systems to be angularly offset from one another, in order to scan an object with the aid of the X-radiation produced by virtue of the fact that the focus/detector systems rotate about a system axis of the CT system;

determining absorption values, for a multiplicity of individual rays in space, from a measured ratio of measured radiation intensity to nonattenuated radiation intensity of the individual rays;

subjecting the measured values to scattered radiation correction; and reconstructing at least one of CT pictures and CT volume data of the object, with the aid of the determined absorption values, radiation intensity of the emitted radiation of each focus/detector system being varied individually as a function of time by a mean value of greater than 50% of the maximum radiation intensity, and, in the respectively assigned detector, the scattered radiation fraction of other nonassigned focus/detector systems being determined by virtue of the fact that at least one of their individual temporal variation of the radiation intensity does not correspond to the assigned focus/detector system, their individual temporal variation of the radiation intensity corresponds to a nonassigned focus/detector system.

2. The method as claimed in claim 1, wherein, only two focus/detector systems with the same scanning frequency are used, the radiation intensities of the two focus/detector systems are varied with the aid of the same function and period, the periods are identical to the period of the scanning frequency of the detectors of the focus/detector systems, and the periods of the variation in the radiation intensities and scanning frequencies of the focus/detector systems are offset from one another by an integral multiple of $\pi/2$ and are synchronous within a focus/detector system.

3. The method as claimed in claim 2, wherein, in the event of a variation in the radiation intensity of the nonassigned focus/detector system by $\pm x$ %, and of a measured difference $\pm y$ % in the radiation intensity between neighboring detector elements, the scattered radiation fraction z % is calculated with the aid of $$z\ \% = \frac{x\ \%}{y\ \%}.$$

4. The method as claimed in claim 2, wherein, referred to the same detector element in the event of a variation in the radiation intensity of the nonassigned focus/detector system by $\pm x$ %, and of a measured radiation intensity $SA_n^i$ of an nth scanning period, the scattered radiation fractions $OS^i_{B \to A}$ are calculated with the aid of:

$$OS^i_{B \to A} = (SA^i_n - SA^i_{n-1}) \cdot \frac{100 - 2 \cdot x}{2 \cdot x}$$

or $$OS^i_{B \to A} = (SA^i_n - SA^i_{n+1}) \cdot \frac{100 - 2 \cdot x}{2 \cdot x}$$

for scanning periods with a positive variation in the radiation intensity, and $$OS^i_{B \to A} = (SA^i_{n-1} - SA^i_n) \cdot \frac{100}{2 \cdot x}$$

or $$OS^i_{B \to A} = (SA^i_{n+1} - SA^i_n) \cdot \frac{100}{2 \cdot x}$$

for scanning periods with a negative variation in the radiation intensity, i representing a serial number for the detector elements considered, and n representing the number of the scanning period.

5. The method as claimed in claim 2, wherein the radiation intensity of the emitted radiation of the focus/detector systems is temporally varied by a mean value of greater than 80% of the maximum radiation intensity.

6. The method as claimed in claim 2, wherein the temporal variation in the radiation intensity of the focus/detector systems runs trapezoidally about the mean value.

7. The method as claimed in claim 2, wherein the temporal variation in the radiation intensity of the focus/detector systems runs sinusoidally about the mean value.

8. The method as claimed in claim 1, wherein in the case of at least two focus/detector systems, the radiation intensities of the focus/detector systems are varied with the same frequencies of different phase, in at least one detector element the variation in the radiation intensity is detected in the respectively indirectly irradiated detector system of at least one focus/detector system with another phase belonging to another focus/detector system, and the scattered radiation fraction in this focus/detector system is determined on the basis of the fraction of the detected radiation with the other phase and of the known fraction of the variation in the generated radiation intensity with this phase.

9. The method as claimed in claim 8, wherein the frequency of the variation in the radiation intensity is lower than the scanning frequencies of the detector systems.

10. The method as claimed in claim 9, wherein the frequency of the variation in the radiation intensity is lower by at least the factor 3, than the scanning frequencies of the detector systems.

11. The method as claimed in claim 8, wherein only two focus/detector systems are used, and wherein the phase shift between the frequencies of the variation in the radiation intensity is an integral multiple of $\pi/2$.

12. The method as claimed in claim 8, wherein, for each focus/detector system, there takes place a monitoring of the direct radiation and a normalization of the measurement to the direct radiation.

13. The method as claimed in claim 1, wherein in the case of at least two focus/detector systems, the radiation intensities of the focus/detector systems are varied with incommensurable frequencies, in at least one detector element, the variation in the radiation intensity is detected in the respectively indirectly irradiated detector system of at least one focus/detector system with another frequency belonging to another focus/detector system, and the scattered radiation fraction in this focus/detector system is determined on the basis of the fraction of the detected radiation with the other phase and of the known fraction of the variation in the generated radiation intensity with this phase.

14. The method as claimed in claim 13, wherein the frequency of the variation in the radiation intensity is lower than the scanning frequencies of the detector systems.

15. The method as claimed in claim 14, wherein the frequency of the variation in the radiation intensity is lower by at least the factor 3, than the scanning frequencies of the detector systems.

16. The method as claimed in claim 13, wherein only two focus/detector systems are used.

17. The method as claimed in claim 1, wherein the temporal variation in the radiation intensity of the focus/detector systems is undertaken by a variation in the tube current.

18. The method as claimed in claim 1, wherein the temporal variation in the radiation intensity of the focus/detector systems is undertaken by a variation in the accelerating voltage.

19. The method as claimed in claim 1, wherein at least one of the determined correction values and the measured values for determining the correction values are averaged over at least one of a number of scanning periods and a number of neighboring detector elements.

20. A computer readable medium including program segments for, when executed on a computer device, causing the computer device to implement the method of claim 1.

21. An X-ray CT system comprising:

at least two focus/detector systems to produce X-radiation in each of the at least two focus/detector systems in an X-ray tube by a tube current with a tube voltage, the focus/detector systems being angularly offset from one another to scan an object with the aid of the X-radiation produced by virtue of the fact that the focus/detector systems rotate about a system axis of the CT system; and a control and arithmetic logic unit for producing tomographic pictures, the control and arithmetic logic unit containing program code, that when executed, carries out a method comprising:
  determining absorption values, for a multiplicity of individual rays in space, from a measured ratio of measured radiation intensity to nonattenuated radiation intensity of the individual rays,
  subjecting the measured values to scattered radiation correction, and
  reconstructing at least one of CT pictures and CT volume data of the object, with the aid of the determined absorption values, radiation intensity of the emitted radiation of each focus/detector system being varied individually as a function of time by a mean value of greater than 50% of the maximum radiation intensity, and, in the respectively assigned detector, the scattered radiation fraction of other nonassigned focus/detector systems being determined by virtue of the fact that at least one of their individual temporal variation of the radiation intensity does not correspond to the assigned focus/detector system, their individual temporal variation of the radiation intensity corresponds to a nonassigned focus/detector system.

22. An X-ray CT system comprising:
at least two focus/detector systems to produce X-radiation in each of the at least two focus/detector systems in an X-ray tube by a tube current with a tube voltage, the focus/detector systems being angularly offset from one another to scan an object with the aid of the X-radiation produced by virtue of the fact that the focus/detector systems rotate about a system axis of the CT system;
means for determining absorption values, for a multiplicity of individual rays in space, from a measured ratio of measured radiation intensity to nonattenuated radiation intensity of the individual rays;
means for subjecting the measured values to scattered radiation correction; and
means for reconstructing at least one of CT pictures and CT volume data of the object, with the aid of the determined absorption values, radiation intensity of the emitted radiation of each focus/detector system being varied individually as a function of time by a mean value of greater than 50% of the maximum radiation intensity, and, in the respectively assigned detector, the scattered radiation fraction of other nonassigned focus/detector systems being determined by virtue of the fact that at least one of their individual temporal variation of the radiation intensity does not correspond to the assigned focus/detector system, their individual temporal variation of the radiation intensity corresponds to a nonassigned focus/detector system.

* * * * *